United States Patent
Morancais et al.

(10) Patent No.: US 6,497,888 B1
(45) Date of Patent: Dec. 24, 2002

(54) PROCESS FOR LIMITING THE PENETRATION INTO THE SKIN AND/OR THE KERATINOUS FIBRES OF AN ACTIVE COSMETIC AND/OR PHARMACEUTICAL AGENT

(75) Inventors: Jean-Luc Morancais, Ozoir la Ferriere (FR); Michel Philippe, Wissous (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/689,636

(22) Filed: Oct. 13, 2000

(30) Foreign Application Priority Data

Oct. 14, 1999 (FR) ............................................. 99 12832

(51) Int. Cl.[7] .......................... A61K 6/00; A61K 31/56; C07C 231/00
(52) U.S. Cl. .......................... 424/401; 554/69; 514/171
(58) Field of Search ........................ 424/401; 554/69; 514/171

(56) References Cited

U.S. PATENT DOCUMENTS

| | | | |
|---|---|---|---|
| 3,821,372 A | | 6/1974 | Vanlerberghe et al. |
| 4,666,711 A | | 5/1987 | Vanlerberghe et al. |
| 4,837,026 A | | 6/1989 | Rajakhyaksha |
| 4,876,249 A | | 10/1989 | Rajadhyaksha |
| 5,030,629 A | | 7/1991 | Rajadhyaksha |
| 5,589,178 A | | 12/1996 | Aubert et al. |
| 5,612,315 A | | 3/1997 | Pikal et al. |
| 5,618,523 A | | 4/1997 | Zysman et al. |
| 5,626,839 A | * | 5/1997 | Scales-Medeiros .......... 424/401 |
| 5,643,899 A | * | 7/1997 | Elias et al. .................. 514/171 |
| 5,656,278 A | * | 8/1997 | Enjolras ...................... 424/401 |
| 5,665,778 A | | 9/1997 | Semeria et al. |
| 5,773,611 A | * | 6/1998 | Zysman et al. ............. 424/401 |
| 5,776,480 A | * | 7/1998 | Candau et al. .............. 424/401 |
| 5,919,960 A | * | 7/1999 | Weber et al. ................. 554/69 |
| 5,959,127 A | * | 9/1999 | Semeria et al. ............... 554/69 |
| 6,099,826 A | | 8/2000 | Ramin |

FOREIGN PATENT DOCUMENTS

| | | |
|---|---|---|
| EP | 0 487 404 | 5/1992 |
| EP | 0 500 437 | 8/1992 |
| EP | 0 647 617 | 4/1995 |
| EP | 0 790 053 | 8/1997 |
| EP | 0 803 242 | 10/1997 |
| EP | 0 920 852 | 6/1999 |
| FR | 1 477 048 | 4/1967 |
| FR | 2 091 516 | 1/1972 |
| FR | 2 315 991 | 1/1977 |
| FR | 2 465 780 | 3/1981 |
| FR | 2 482 128 | 11/1981 |
| FR | 2 740 031 | 4/1997 |
| FR | 2 767 056 | 2/1999 |
| WO | WO 92/06179 | 4/1992 |
| WO | WO 93/01571 | 1/1993 |

OTHER PUBLICATIONS

Francis Szoka, Jr. et al., "Procedure for Preparation of Liposomes With Large Internal Aqueous Space and High capture by Reverse–Phase Evaporation", Proc. Natl. Acad. Sci. USA, vol. 75, No. 9, Sep. 1978, pp. 4194–4198.
English language Derwent Abstract of EP 0 790 053.
English language Derwent Abstract of FR 2 315 991.
English language Derwent Abstract of FR 2 740 031.
English language Derwent Abstract of FR 2 767 056.

* cited by examiner

Primary Examiner—Michael G. Hartley
Assistant Examiner—Michael A. Willis
(74) Attorney, Agent, or Firm—Finnegan, Henderson, Farabow, Garrett & Dunner, L.L.P.

(57) ABSTRACT

A process, composition, and kit for limiting the penetration into the skin and/or the keratinous fibers of at least one cosmetically and/or pharmaceutically active agent present in a base cosmetic and/or pharmaceutical composition for topical application and in particular for reducing the rate of penetration into the skin and/or the keratinous fibers of the active agent(s). The process includes the joint use, with the base composition, of an effective amount of a dispersion of vesicles in a medium, the vesicles comprising at least one ceramide of formula (I):

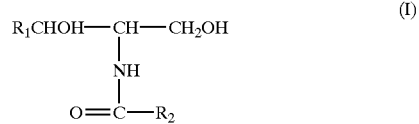

(I)

Figure 1A:
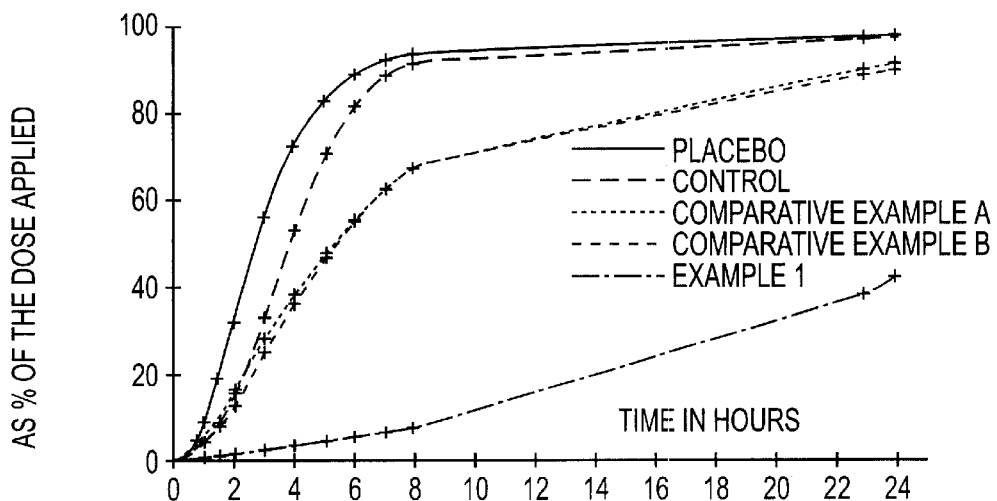

wherein $R_1$ is chosen from saturated and unsaturated, linear and branched $C_1$–$C_{32}$ alkyl groups optionally substituted by at least one hydroxyl group, wherein said at least one hydroxyl group is optionally esterified by a group chosen from $C_1$–$C_{35}$ acyls; and $R_2$ is chosen from saturated and unsaturated, linear and branched $C_1$–$C_{50}$ alkyl groups optionally substituted by at least one hydroxyl groups, and wherein said at least one hydroxyl group is optionally esterified by a group chosen from $C_1$–$C_{30}$ acyls.

37 Claims, 2 Drawing Sheets

PROCESS FOR LIMITING THE PENETRATION INTO THE SKIN AND/OR THE KERATINOUS FIBRES OF AN ACTIVE COSMETIC AND/OR PHARMACEUTICAL AGENT

The present invention relates generally to a process for limiting the penetration into the skin and/or the keratinous fibres of at least one cosmetically and/or pharmaceutically active agent present in a base cosmetic and/or pharmaceutical composition for topical application and in particular for reducing the rate of penetration into the skin and/or the keratinous fibres of the active agent(s).

Numerous families of compounds are known which have the property of activating the penetration into the skin or the keratinous fibres of an active agent present in a cosmetic and/or pharmaceutical composition. Thus, U.S. Pat. No. 4,960,771 discloses the use, in cosmetic or pharmaceutical compositions, of oxazolidinone derivatives for increasing the penetration of active agents in the broadest sense. The use of amides for increasing this penetration is disclosed in U.S. Pat. No. 5,162,315.

U.S. Pat. Nos. 4,837,026, 4,876,249 and 5,030,629 disclose cyclic derivatives which promote the penetration of active agents.

On the other hand, very few families of compounds are known which possess the reverse activity, that is to say effectively reducing the penetration of an active agent of a cosmetic and/or pharmaceutical composition into the skin and/or the keratinous fibres.

However, some oxazolidinone derivatives exhibit this property.

It would be desirable to have available compounds or formulations having properties of reducing the penetration into the skin and/or the keratinous fibres of active agents of cosmetic and/or pharmaceutical compositions.

This is because, for certain cosmetic and/or pharmaceutical formulations for application to the skin and/or the keratinous fibres, it is highly desirable to reduce, slow down or indeed even eliminate the penetration of an active agent of the formulation into the substrate, skin or keratinous fibres to which the cosmetic and/or pharmaceutical formulation is applied, either for reasons of safety or for reasons of effectiveness.

Thus, for reasons of effectiveness, it may be important to reduce the penetration of dyes or of sunscreens into the keratinous fibres and/or the skin.

In the case of sunscreens, the protective effect of which on the skin decreases according to their penetration into the skin, it is desirable to slow down, indeed optionally even eliminate, their penetration into the skin in order to increase the effectiveness thereof.

It would thus be desirable to have available an agent which, used with a base cosmetic and/or pharmaceutical composition comprising at least one cosmetically and/or therapeutically active agent, reduces, indeed even eliminates, the penetration into the skin and/or the keratinous fibres of the cosmetically and/or therapeutically active agent.

The above aim is achieved according to the invention by the joint use, with a base cosmetic and/or pharmaceutical composition comprising at least one cosmetically and/or pharmaceutically active agent, of an effective amount of a dispersion of vesicles in a medium, the vesicles comprising at least one ceramide of formula (I):

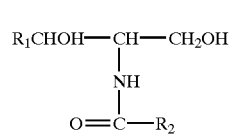

in which $R_1$ is chosen from saturated and unsaturated, linear and branched $C_1$–$C_{32}$, preferably $C_9$–$C_{25}$, alkyl groups optionally substituted by at least one hydroxyl group, wherein the at least one hydroxyl group is optionally esterified by a group chosen from $C_1$–$C_{35}$, preferably $C_8$–$C_{28}$, acyl groups, and $R_2$ is chosen from saturated and unsaturated, linear and branched $C_1$–$C_{50}$, preferably $C_6$–$C_{35}$, alkyl groups optionally substituted by at least one hydroxyl group, and wherein the at least one hydroxyl group is optionally esterified by a group chosen from $C_1$–$C_{30}$, preferably $C_6$–$C_{24}$, acyl groups.

The medium in which the vesicles are dispersed is essentially an aqueous medium. This means that the medium is sufficiently aqueous so that the vesicles can be dispersed therein.

A subject-matter of the invention is therefore a process for limiting, indeed even eliminating, the penetration into the skin and/or the keratinous fibres of at least one cosmetically and/or pharmaceutically active agent present in a base cosmetic and/or dermal pharmaceutical composition, characterized in that it consists in using, jointly with the base composition, an effective amount of the dispersion of vesicles defined above.

The term "joint use of the base composition and of the dispersion of vesicles" is understood to mean either the addition of the effective amount of the dispersion of vesicles directly to the base composition before use, such as by application in the form of a film on the skin and/or the keratinous fibres, or the successive application to the skin and/or to the keratinous fibres, in the form of films, of an effective amount of the dispersion of vesicles, followed by the base composition.

The term "effective amount of the dispersion of vesicles" is understood to mean an amount of the dispersion sufficient to produce a significant effect in limiting the penetration, in particular the rate of penetration, of the active agent or agents of the base composition.

Another subject-matter of the present invention is a cosmetic or pharmaceutical composition which includes at least one cosmetically or pharmaceutically active agent, characterized in that it additionally comprises a dispersion of vesicles as defined above in an amount which is effective in limiting the penetration of the active agent or agents into the skin and/or the keratinous fibres.

The at least one ceramide of the formula (I) is chosen from known compounds. These ceramides and their processes of preparation are disclosed, inter alia, in European Patents EP-500,437, EP-647,617 and EP-790,053, the disclosures of which are specifically incorporated by reference herein.

The dispersion of vesicles can also comprise a mixture of ceramides of formula (I) and/or a stereoisomeric mixture of ceramides of formula (I).

Mention may be made, among the preferred ceramides of formula (I), of 2-(oleoylamino)octadecane-1,3-diol, 2-(lineoylamino) octadecane-1,3-diol, 2-[(2'-hydroxyhexadecanoyl)amino]octadecane-1,3-diol, 2-[(2'-hydroxydecosanoyl)amino]octadecane-1,3-diol, 2-[(D,L-mandeloyl)amino]octadecane-1,3-diol and oleyl chloride.

The particularly preferred ceramide is 2-[(2'-hydroxyhexadecanoyl)amino]octadecane-1,3-diol.

The dispersion of vesicles can comprise at least one second lipids other than the at least one ceramide of formula (I).

The at least one second lipid used in combination with the at least one ceramide of formula (I) in the dispersion of vesicles can be any lipid, other than the at least one ceramide of formula (I) of the dispersion, which makes possible the formation of vesicles and which does not harm the property of limiting penetration of the cosmetically and/or pharmaceutically active agent or agents of the dispersion.

A representative at least one second lipid capable of being used in combination with the at least one ceramide of formula (I), is chosen from alcohols and diols with a chain comprising 8–32 carbon atoms, preferably 12–30 carbon atoms, steroids, such as cholesterol, phospholipids, cholesteryl sulphate and phosphate, amines with a chain comprising 8–32 carbon atoms, preferably 12–30 carbon atoms, and their quaternary ammonium derivatives, dihydroxyalkylamines, polyoxyethylenated amines with a chain comprising 8–32 carbon atoms, preferably 12–30 carbon atoms, esters of aminoalcohols with a chain comprising 8–32 carbon atoms, preferably 12–30 carbon atoms, their salts and quaternary ammonium derivatives, phosphoric esters of alcohols with a chain comprising 8–32 carbon atoms, preferably 12–30 carbon atoms, such as dicetyl hydrogen phosphate and its sodium salt, alkyl sulphates, such as sodium cetyl sulphate, acids with a chain comprising 8–32 carbon atoms, preferably 12–30 carbon atoms, in the form of salts, and lipids of the type of those disclosed in Patents FR-2,315,991, 1,477,048 and 2,091,516 or in International Patent Application WO 93/01571, the disclosures of all of which are specifically incorporated by reference herein.

The term "lipid" is understood to mean any compound having a chain chosen from saturated and unsaturated, linear and branched, lipophilic chains comprising in particular 8 to 32 carbon atoms, preferably 12 to 30 carbon atoms, for example, oleyl, lanolyl, tetradecyl, hexadecyl, isostearyl, lauryl and alkylphenyl chains. Generally, but not necessarily, these lipids furthermore comprise a hydrophilic chain, which can be an ionic or nonionic group. Mention may be made, as nonionic groups, of groups derived from polyethylene glycol. Use may also be made, as second lipids, of polyglycerol ethers, such as those disclosed in Patents FR-1,477,048, 2,091,516, 2,465,780 and 2,482,128, the disclosures of all of which are specifically incorporated by reference herein.

Use may be made, as ionic groups, of groups chosen from amphoteric, anionic and cationic groups.

The at least one second lipid which can be used in the dispersion of vesicles are representatively chosen from glycolipids, such as lactosylceramide, galactocerebroside, gangliosides and trihexosylceramide, and phospholipids, such as phosphatidylglycerol, phosphatidylinositol, phosphatidylcholine and sphingomyelin.

The at least one second lipid according to the invention can also be representatively chosen from cholesteryl salts, such as cholesteryl sulphates.

The cholesteryl sulphates can be representatively chosen from alkaline sulphates, such as sodium sulphate.

The ratio by weight of the at leasyt one ceramide of formula (I) to the possible at least one second lipid in the dispersion of vesicles generally varies from 80/20 to 20/80, such as from 70/30 to 30/70.

The total concentration of at least one ceramide of formula (I) and the at least one second lipid in the dispersion of vesicles generally varies from 0.05 to 15%, such as from 0.5 to 7.5%, with respect to the total weight of the dispersion.

The dispersion of vesicles can also comprise conventional adjuvants, such as other lipids which are different from the at least one ceramide of formula (I) and the at least one second lipid, emulsifiers, thickeners and solvents.

Representative adjuvants which can be present in the dispersion of vesicles can be chosen from fatty substances, such as mineral, animal and vegetable oils and waxes, fatty acids, fatty acid esters, such as triglycerides of fatty acids having from 6 to 18 carbon atoms and fatty alcohols; emulsifiers, such as oxyethylenated fatty alcohols and polyglycerol alkyl ethers; and solvents, such as lower monoalcohols or polyalcohols comprising 1 to 6 carbon atoms or water.

Specific mono- and polyalcohols are chosen from ethanol, isopropanol, propylene glycol, glycerol and sorbitol.

Representative fatty substances include mineral oils, such as liquid petrolatum; animal oils, such as whale, seal, menhaden, halibut liver, cod, tuna, tortoise, ox hoof, horse hoof, sheep hoof, mink, otter and marmot oils and the like; and vegetable oils, such as almond, wheat germ, olive, maize germ, jojoba, sesame, sunflower, palm, walnut, karite, shorea, macadamia and blackcurrant seed oils and the like.

Representative fatty acid esters can be chosen from esters of saturated and unsaturated $C_{12}$ to $C_{22}$ acids and of lower alcohols, such as isopropanol and glycerol, of saturated and unsaturated, linear and branched, $C_8$ to $C_{22}$ fatty alcohols and of $C_{10}$–$C_{22}$ 1,2-alkanediols.

Representative fatty substances can be chosen from petrolatum, paraffin, lanolin, hydrogenated lanolin, tallow, acetylated lanolin and silicone oils.

Representative waxes can be chosen from Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, Ca, Mg and Al oleates, myristates, linoleates and stearates.

Representative fatty alcohols can be chosen from lauryl, cetyl, myristyl, stearyl, palmityl and oleyl alcohols and Guerbet alcohols, such as 2-octyldodecanol, 2-decyltetradecanol and 2-hexyldecanol.

Representative emulsifying agents can be chosen from polyoxyethylenated fatty alcohols, such as lauryl, cetyl, stearyl and oleyl alcohols comprising from 2 to 20 mol of ethylene oxide and from polyglycerol alkyl ethers, such as $C_{12}$–$C_{18}$ alcohols comprising from 2 to 10 mol of glycerol.

It can also be useful to use thickeners, such as cellulose derivatives, polyacrylic acid derivatives, guar gum, locust bean gum or xanthan gum.

The concentration of these adjuvants in the vesicular dispersion generally varies from 0.1 to 20% with respect to the total weight of the dispersion.

The continuous phase of the vesicular dispersion can be representatively chosen from aqueous/alcoholic solutions, water and saline aqueous solutions.

The vesicles generally have a diameter which varies from 0.05 to 5 mm.

The cosmetic and/or pharmaceutical compositions of the process of the invention are all conventional cosmetic and/or pharmaceutical compositions incorporating at least one cosmetically and/or pharmaceutically active agent.

The term "cosmetically and/or pharmaceutically active agent"(or "active agent") is understood to mean any compound or mixture of compounds having a cosmetic and/or pharmaceutical activity.

Representative active agents can be chosen from moisturizing agents, humectants, such as glycerol, sorbitol, pentaerythritol and pyrrolidonecarboxylic acid and its salts; artificial tanning agents, such as dihydroxyacetone, erythrulose, glyceraldehyde and γ-dialdehydes for example tartaric aldehyde; water-soluble and liposoluble colorants; water-soluble and liposoluble sunscreens; UV stabilizers; antiperspirants; deodorants; astringents; freshening products; tonics; cicatrizing agents; keratolytic agents; depilatory agents; fragrances and scented waters; plant tissue extracts, such as polysaccharides; antidandruff agents; antiseborrhoeic agents; oxidizing agents, such as bleaching agents, for example aqueous hydrogen peroxide solution; reducing agents, such as thioglycolic acid and its salts; vitamins, such as vitamins E, F or A and their esters; hormones, enzymes, such as superoxide dismutase; antifungals; anti-inflammatories, such as hydrocortisone; antibiotics; bactericides; cytotoxic and antitumour agents; substances intended to improve the condition of dry or senile skin; tocopherols; retinoic acid; antioxidants; essential fatty acids; glycyrrhetinic acid and carotenoids.

The cosmetic and/or dermatological compositions targeted by the present invention can, of course, comprise at least one additional, sunscreen chosen from hydrophilic and lipophilic sunscreens which are active in the UVA and/or UVB regions (absorbers). These additional screening agents can be chosen in particular from cinnamic derivatives, salicylic derivatives, benzylidenecamphor derivatives, benzotriazole derivatives, benzimidazole derivatives, triazine derivatives, benzylmalonic derivatives, b,b-diphenylacrylate derivatives, p-aminobenzoic acid derivatives, and the screening polymers and silicones disclosed in Application WO/93 04665, the disclosure of which is specifically incorporated by reference. Other examples of organic screening agents are given in Patent Application EP-A-0,487,404, the disclosure of which is specifically incorporated by reference.

The preferred active agents are colorants and sunscreens.

The proportion of active agent in the base composition depends on the nature of the active agent and on the desired activity. In general, the at least one active agent represents from 0.05 to 25%, such as 0.5 to 15%, by weight of the base composition.

The base composition can comprise other conventional adjuvants in the conventional proportions. In particular, it can comprise lipids, in particular lipids other than the at least one ceramide of formula (I) described in connection with the vesicular dispersion.

In particular, the base composition can comprise a liquid phase dispersed in an aqueous phase, the constituent(s) of which can be chosen from the group formed by oils, such as esters of fatty acids and of polyols and esters of fatty acids and of branched alcohols of formula $R_3$—COO—$R_4$, in which formula $R_3$ is chosen from residues of higher $C_7$–$C_{19}$ fatty acids and $R_4$ is chosen from branched $C_3$–$C_{20}$ hydrocarbonaceous chains; hydrocarbons, such as hexadecane or liquid paraffin; perhydrosqualene; halogenated hydrocarbons, such as perfluorodecahydronaphthalene; perfluorotributylamine; polysiloxanes; esters of organic acids; ethers and polyethers.

This liquid phase can include at least one liposoluble active agent, such as liposoluble sunscreens, tocopherols, vitamins E and F, vitamin A and its esters, retinoic acid, antioxidants, essential fatty acids, glycyrrhetinic acid, keratolytic agents and carotenoids.

The active agents can be dissolved or in the form of a dispersion in the cosmetically and/or pharmaceutically acceptable medium of the base composition. In particular, the active agents can be in the form of a dispersion of vesicles in the medium of the base composition. In the case of water-soluble active agents, they can be present in an aqueous phase encapsulated in vesicles composed of one or more lipids. In the case of liposoluble active agents, they are then found incorporated in the lipid layers of the vesicles.

As indicated above, in the process of the invention, the dispersion of vesicles can be incorporated in the base composition. The incorporation of the dispersion of vesicles can take place either by preparing the dispersion of vesicles and the base composition separately and by combining them in an appropriate fashion or by forming the dispersion of vesicles directly in the base composition during the preparation of the base composition (in situ formation).

In the case of the introduction of a preprepared dispersion of vesicles into a base composition, the amount of dispersion introduced is such that the concentration of the at least one ceramide of formula (I) and of the at least one second lipid in the final composition varies from 0.05 to 15% by weight, such as from 0.5 to 7.5% by weight.

Likewise, when the dispersion of vesicles is formed in situ in the base composition, the total amount of the at least one ceramide of formula (I) and of the at least one second lipid which is introduced is such that the concentration of the at least one ceramide of formula (I) and of the at least one second lipid represents from 0.05 to 15%, such as from 0.5 to 7.5%, by weight of the final composition. In all cases, the ratio by weight of the at least one ceramide of formula (I) to the at least one second lipid varies from 80/20 to 20/80, such as 70/30 to 30/70, in the final compositions.

In the case of the formation of the dispersion of vesicles in situ, during the formulation of the base composition, the at least one active agent can be incorporated in the vesicles of the dispersion of vesicles either in the form of an aqueous solution encapsulated in the lipid phase of the vesicles or in the lipid phase of the vesicles, if the active agent is liposoluble.

The joint use of the dispersion of vesicles and of the base composition can take place by applying first of all the dispersion of vesicles to the skin and/or the keratinous fibres, in order to form a film, and by then applying the base composition comprising the at least one active agent to the film formed.

In this form of use, the dispersion of vesicles and the base composition can be provided in the form of a kit, that is to say be packaged in separate containers present in the same packaging.

The vesicles can be obtained in particular according to the process disclosed in French Patent 2,315,991 of L'Oréal, S. A., the disclosure of which is incorporated by reference, according to which a dispersion of vesicles, composed of organized molecular layers including an aqueous phase to be encapsulated, is prepared by bringing into contact, on the one hand, at least one lipid compound, in particular of formula (I), in combination with at least one other lipid, as defined above and, on the other hand, the aqueous phase to be encapsulated in the vesicles, by stirring in order to ensure mixing and to obtain a lamellar phase, by subsequently adding a dispersion liquid in an amount greater than the amount of lamellar phase obtained, and by vigorously shaking for a period of time ranging from 15 minutes to 3 hours approximately.

The ratio by weight of the aqueous dispersion phase which is added to the lamellar phase, which is dispersed, can be from 2:1 to 100:1; the dispersion phase and the aqueous phase to be encapsulated can be isoosmotic.

Stirring can be carried out by means of a shaker. The process can, for example, be carried out at a temperature from 30° to 120° C.

The dispersion can subsequently be treated by ultrasound and/or be homogenized by a conventional mechanical means.

Another preparation process can comprise using the process known as the REV (reverse-phase evaporation vesicle) process described in Proc. Natl. Acad. Sci. USA., Vol. 75, No. 9, pages 4194–4198 (1978), by Szoka & Papahadjopoulos, the disclosure of which is incorporated by reference.

The process of the invention can be applied in the field of caring for the skin and/or the keratinous fibres, such as the hair, and in the make-up field. In particular, it can advantageously be applied in the field of protecting against sunlight, where, by slowing down penetration of the sunscreen into the skin, it prolongs the protective activity of the screening agent, and in the field of colouring the hair, where it restricts the penetration of colorants into the skin and/or the scalp.

In the following examples, which illustrate the present invention, all percentages and parts are expressed by weight, unless otherwise indicated.

EXAMPLE 1

A dispersion of vesicles having properties of limiting the penetration of active agents was prepared by dissolving 0.75 g of 2-[(2'-hydroxyhexadecanoyl)-amino]octadecane-1,3-diol and 0.50 g of cholesteryl sodium sulphate in 40 ml of a 50/50 mixture of $CH_2Cl_2/CH_3OH$ present in a 100 ml round-bottomed flask placed in an ultrasound tank at 40° C.

After dissolution, the solvents are removed under vacuum at 40° C.

A 0.1 M Tris buffer solution, adjusted to pH=6.75, is then added, so as to obtain approximately 15 g of preparation comprising 5% by weight of lipids.

The preparation is shaken at 60° C. for 1 hour and is then brought back to room temperature.

7.5 to 10 g of dispersion are then treated with ultrasound, using a Sonifier B30 device from Branson Sonic (I=5.50% of the cycle), 6 times for 1 minute, with a rest time of approximately 3 minutes between the treatments, in order to return to 60° C.

A 5% by weight 60/40 ceramide (I) second lipid vesicular dispersion is obtained which is suitable for the process of the invention and which has the following characteristics:

pH=6.9

Mean diameter of the vesicles: 152 nm (at 25° C.; Coulter N4 device; sample diluted to 0.003% by weight of lipids with Tris/HCl buffer filtered through a 0.8 mm filter).

Comparative Example A 0.37 g of a lipid of formula:

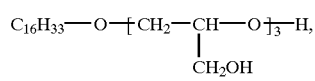

0.36 g of cholesterol and 0.04 g of sodium dicetyl phosphate are dissolved at 40° C. in 30 ml of $CH_2Cl_2$ present in a 100 ml round-bottomed flask placed in an ultrasound tank.

All the solvent is removed at 40° C. and a 0.1M Tris buffer solution, adjusted to pH=6.75 with HCl, is added in order to obtain approximately 15 g of preparation comprising 5% by weight of lipids.

The preparation is shaken at 70° C. for 2 hours.

The preparation is brought back to room temperature and is then treated with ultrasound as in Example 1.

A dispersion of vesicles (niosome) is obtained which has the following characteristics:

pH=6.6

Mean diameter of the particles: 152 nm (measured as in Example 1).

Comparative Example B 0.61 g of Phospholipon® 80 (mixture of phospholipids based on phosphatidylcholine) and 0.15 g of cholesterol are dissolved at 40° C. in 100 ml of $CH_2Cl_2$ present in a 100 ml round-bottomed flask placed in an ultrasound tank.

The solvents are removed at 40° C. and a Tris buffer solution, adjusted to pH=6.75 with HCl, is added in order to obtain approximately 15 g of preparation.

The preparation is shaken under $N_2$ at 40° C. for 2 hours and is then brought back to room temperature.

The preparation, in fractions of 7.5 to 10 g, is then treated with ultrasound 6 times for 1 minute, with a rest time of approximately 5 minutes between the treatments, in order to return to 3–4° C. (Sonifier B30; I=5.50% of the cycle; bath at 0° C.).

A dispersion (liposome) is obtained which has the following characteristics:

pH=6.3

Mean diameter of the particles: 140 nm (Coulter N4; sample comprising 0.006% by weight of lipids).

150 ml of the above dispersions were applied to samples of Episkin® reconstructed skin at the 13- and 20-day stage (these biomaterials comprise a collagen membrane and their processes of manufacture are disclosed in Patent EP 502, 172) and were left to act for 20 hours. A composition comprising $^{14}C$-benzoic acid (12,500 nmol/125 ml 80/20 glycerol/water) was then applied and the degree of penetration of the benzoic acid into the reconstructed skin after 24 hours, its kinetics of penetration through this skin and the amounts unpenetrated at the end of the contact time of the composition comprising benzoic acid (24 hours) were measured (as % of the amount of benzoic acid applied).

The degree of penetration resulting from the direct application of the active agent composition (control) and with the use under the same conditions of a placebo instead of the dispersions of the examples have also been shown, by way of comparison. The placebo comprised the Tris/HCl buffer solution.

Figure 1B:
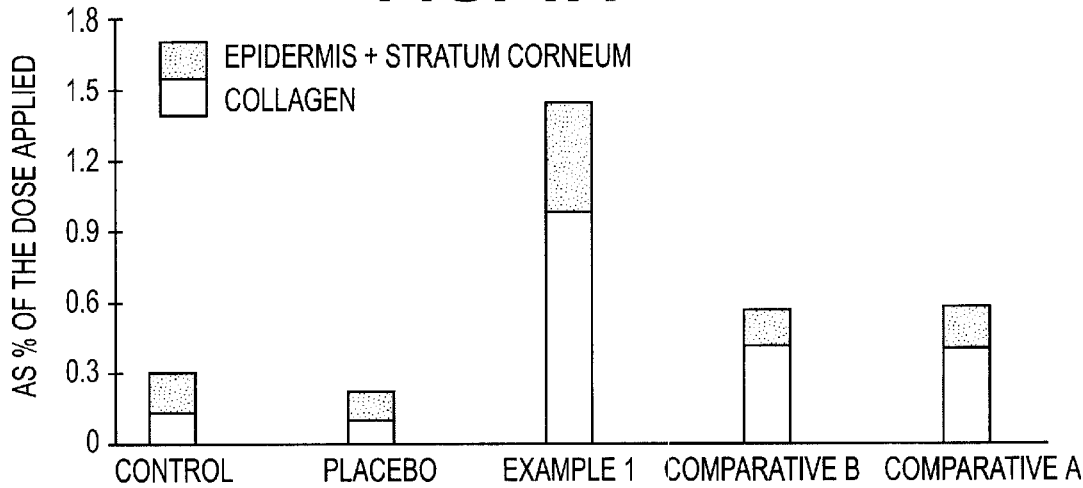
Figure 1C:
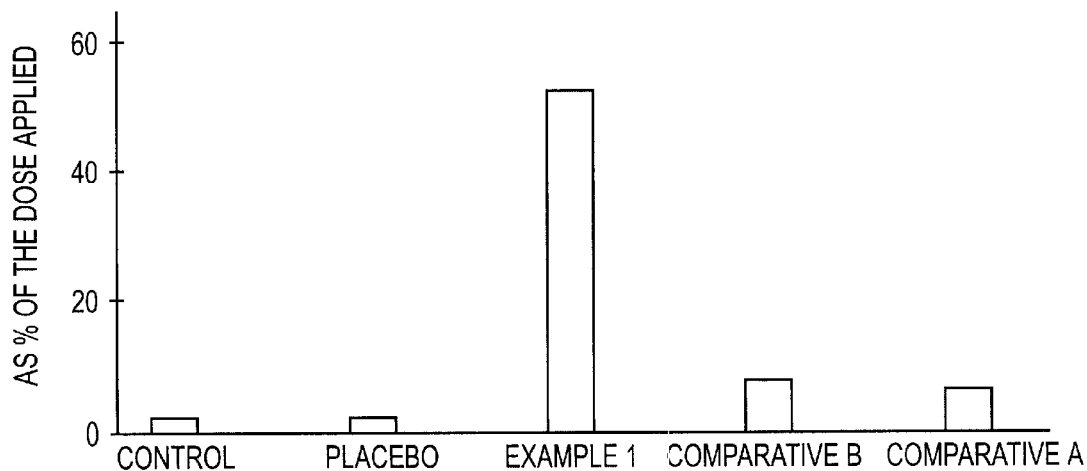
Figure 2A:
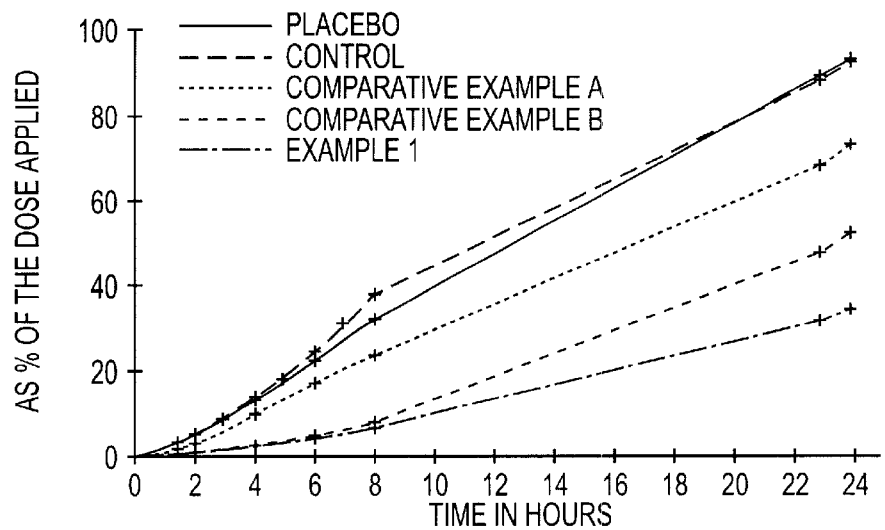
Figure 2B:
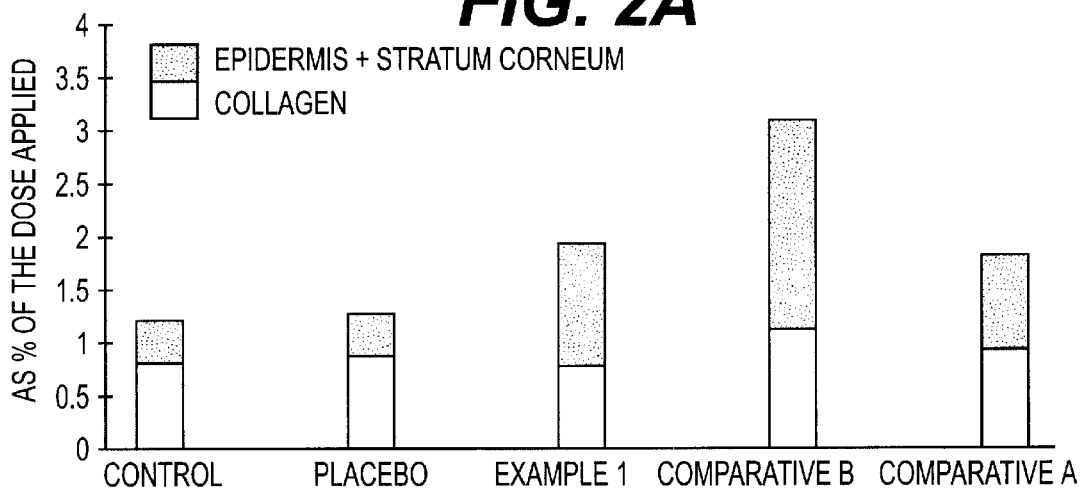
Figure 2C:
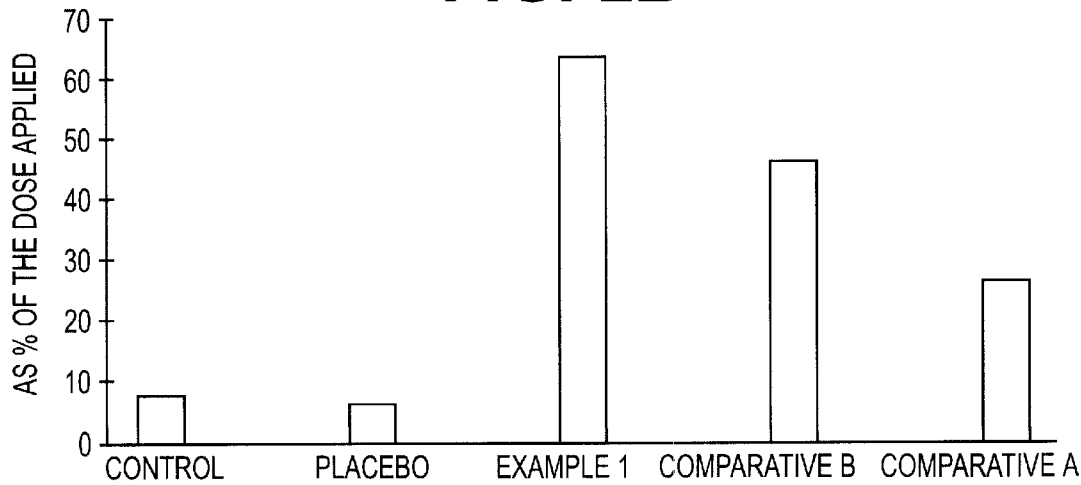

The results are given in FIGS. 1 (Episkin®, 13 days) and 2 (Episkin®,20 days), which represent the level of the active agent (as % of the amount applied) recovered:

as a function of time after passing through the reconstructed skin (A);

in the same reconstructed skin at the end of the contact time of the applied composition (B);

and at the surface, that is to say in the contact solution, at the end of contact (24 hours, C).

The figures clearly show that the use according to the invention of the dispersion of vesicles of Example 1 significantly restricts the penetration of the benzoic acid, not only with respect to the control but also with respect to Comparatives A and B.

EXAMPLES 2 AND 3

Dispersions of vesicles were introduced into the base compositions. The formulations obtained are given in the table below.

|  | Parts by weight | |
| --- | --- | --- |
|  | Ex. 2 | Ex. 3 |
| Glyceryl stearate | 2.5 | — |
| Mineral oil | 6.2 | — |
| Isopropyl myristate | 3 | — |
| Cetyl alcohol | 7 | — |
| PEG-50 stearate | 2.5 | — |
| Cholesteryl Na sulphate | — | — |
| Xanthan gum | — | 1.5 |
| Vesicular dispersion No. 1 | 33.3 | 33.3 |
| Methylparaben | 0.3 | — |
| Water | 45.2 | 65.2 |

The vesicular dispersion No. 1 corresponds to a 60/40 2-(2'-hydroxyhexadecanol)aminooctadecane-1,3-diol/cholesteryl Na sulphate mixture, as a 5% aqueous dispersion, comprising 0.25% by weight of methylparaben and buffered with a Tris 0.1M buffer solution adjusted to pH 7.2 with 2M HCl.

The vesicular dispersion No. 1 was obtained in a similar way to the dispersion of Example 1.

What is claimed is:

1. A process for limiting penetration into at least one of skin and keratinous fibres of at least one active agent, chosen from colorants and sunscreens, present in a base composition, chosen from cosmetic and pharmaceutical base compositions, comprising jointly applying to said at least one of skin and keratinous fibers said base composition and an effective amount of a dispersion of vesicles in a medium, said vesicles comprising at least one ceramide of formula (I):

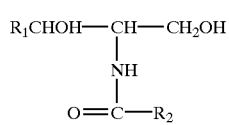

(I)

wherein $R_1$ is chosen from saturated and unsaturated, linear and branched $C_1$–$C_{32}$ alkyl groups optionally substituted by at least one hydroxyl group, wherein said at least one hydroxyl group is optionally esterified by a group chosen from $C_1$–$C_{35}$ acyls; and $R_2$ is chosen from saturated and unsaturated, linear and branched $C_1$–$C_{50}$ alkyl groups optionally substituted by at least one hydroxyl groups, and wherein said at least one hydroxyl group is optionally esterified by a group chosen from $C_1$–$C_{30}$ acyls.

2. The process according to claim 1, wherein $R_1$ is chosen from saturated and unsaturated, linear and branched $C_9$–$C_{25}$ alkyl groups optionally substituted by at least one hydroxyl group, wherein said at least one hydroxyl group is optionally esterified by a group chosen from $C_1$–$C_{35}$ acyls.

3. The process according to claim 1, wherein $R_1$ is chosen from saturated and unsaturated, linear and branched $C_1$–$C_{32}$ alkyl groups optionally substituted by at least one hydroxyl group, wherein said at least one hydroxyl group is optionally esterified by a group chosen from $C_8$–$C_{28}$ acyls.

4. The process according to claim 1, wherein $R_2$ is chosen from saturated and unsaturated, linear and branched $C_6$–$C_{35}$ alkyl groups optionally substituted by at least one hydroxyl group, wherein said at least one hydroxyl group is optionally esterified by a group chosen from $C_1$–$C_{30}$ acyls.

5. The process according to claim 1, wherein $R_2$ is chosen from saturated and unsaturated, linear and branched $C_1$–$C_{50}$ alkyl groups optionally substituted by at least one hydroxyl group, wherein said at least one hydroxyl group is optionally esterified by a group chosen from $C_6$–$C_{24}$ acyls.

6. The process according to claim 1, wherein the at least one ceramide of formula (I) is chosen from:
2-(oleoylamino)octadecane-1,3-diol,
2-(lineoylamino)octadecane-1,3-diol, 2-[(2'-hydroxyhexadecanoyl)amino]octadecane-1,3-diol,
2-[(2'-hydroxydecosanoyl)amino]octadecane-1,3-diol,
2-[(D,L-mandeloyl)amino]octadecane-1,3-diol and oleyl chloride.

7. The process according to claim 6, wherein the at least one ceramide is 2-[(2'-hydroxyhexadecanoyl)amino]octadecane-1,3-diol.

8. The process according to claim 1, wherein the vesicles comprise at least one of a mixture of ceramides of formula (I) and a stereoisomeric mixture of ceramides of formula (I).

9. The process according claim 1, wherein the vesicles further comprise at least one second lipid which is different from the at least one ceramide of formula (I).

10. The process according to claim 9, wherein the at least one second lipid is chosen from:
alcohols and diols having chains comprising from 8 to 32 carbon atoms;
amines having chains comprising from 8 to 32 carbon atoms and their quaternary ammonium derivatives;
dihydroxyalkylamines;
polyoxyethylenated amines having chains comprising from 8 to 32 carbon atoms;
esters of aminoalcohols having chains comprising from 8 to 32 carbon atoms, their salts and quaternary ammonium derivatives;
phosphoric esters of alcohols having chains comprising from 8 to 32 carbon atoms;
alkyl sulphates; and
acids having chains comprising from 8 to 32 carbon atoms, in the form of salts.

11. The process according to claim 10, wherein the at least one second lipid is chosen from alcohols and diols having chains comprising from 12 to 30 carbon atoms.

12. The process according to claim 9, wherein the at least one second lipid is chosen from cholesterol, phospholipids, cholesteryl sulphate and cholesteryl phosphate.

13. The process according to claim 9, wherein the at least one second lipid is chosen from amines having chains comprising from 8 to 32 carbon atoms.

14. The process according to claim 9, wherein the at least one second lipid is chosen from amines having chains comprising from 12 to 30 carbon atoms, and their quaternary ammonium derivatives.

15. The process according to claim 9, wherein the at least one second lipid is chosen from polyoxyethylenated amines having chains comprising from 12 to 30 carbon atoms.

16. The process according to claim 9, wherein the at least one second lipid is chosen from esters of aminoalcohols having chains comprising from 12 to 30 carbon atoms, and their salts and quaternary ammonium derivatives.

17. The process according to claim 9, wherein the at least one second lipid is chosen from phosphoric esters of alcohols having chains comprising from 12 to 30 carbon atoms.

18. The process according to claim 9, wherein the at least one second lipid is chosen from dicetyl hydrogen phosphate and its sodium salt.

19. The process according to claim 9, wherein the at least one second lipid is sodium cetyl sulphate.

20. The process according to claim 9, wherein the at least one second lipid is chosen from acids with a chain comprising from 12 to 30 carbon atoms, in the form of salts.

21. The process according to claim 9, wherein the at least one second lipid is chosen from cholesteryl alkali metal sulphates.

22. The process according to claim 9, wherein the at least one second lipid is cholesteryl sodium sulphate.

23. The process according to claim 9, wherein the ratio by weight of the at least one ceramide of formula (I) to the at least one second lipid in the vesicles ranges from 80/20 to 20/80.

24. The process according to claim 9, wherein the ratio by weight of the at least one ceramide of formula (I) to the at least one second lipid in the vesicles ranges from 70/30 to 30/70.

25. The process according to claim 9, wherein a total concentration of the at least one ceramide of formula (I) and the at least one second lipid ranges from 0.05 to 15%, with respect to a total weight of the dispersion of vesicles.

26. The process according to claim 9, wherein a total concentration of the at least one ceramide of formula (I) and the at least one second lipid ranges from 0.5 to 7.5%, with respect to a total weight of the dispersion of vesicles.

27. The process according to claim 9, wherein the dispersion of vesicles additionally comprises at least one adjuvant chosen from emulsifiers, thickeners, solvents, and lipids which are different from the at least one ceramide of formula (I) and from the at least one second lipid.

28. The process according to claim 1, wherein the colorants are chosen from water-soluble and lipo-soluble colorants; and the sunscreens are chosen from water-soluble and liposoluble sunscreens.

29. The process according to claim 1, wherein the at least one active agent is present in the base composition at a concentration ranging from 0.05 to 25% by weight with respect to a total weight of the base composition.

30. The process according to claim 1, wherein the at least one active agent is present in the base composition at a concentration ranging from 0.05 to 15% by weight with respect to a total weight of the base composition.

31. The process according to claim 1, wherein the jointly applying of the dispersion of vesicles and the base composition comprises:
incorporating the dispersion of vesicles in the base composition to form a final composition; and
applying the final composition to said at least one of skin and keratinous fibres.

32. The process according to claim 31, wherein the dispersion of vesicles further comprises at least one second lipid which is different from the at least one ceramide of formula (I), and further wherein an amount of the dispersion of vesicles incorporated in the base composition is such that a total concentration of the at least one ceramide of formula (I) and the at least one second lipid in the final composition ranges from 0.05 to 15% by weight of the final composition.

33. The process according to claim 31, wherein the dispersion of vesicles further comprises at least one second lipid which is different from the at least one ceramide of formula (I), and further wherein an amount of the dispersion of vesicles incorporated in the base composition is such that a total concentration of the at least one ceramide of formula (I) and the least one second lipid in the final composition ranges from 0.5 to 7.5% by weight of the final composition.

34. The process according to claim 1, wherein the jointly applying of the dispersion of vesicles and the base composition comprises:
forming the dispersion of vesicles in situ during the formulation of the base composition to form a final composition; and
applying the final composition to said at least one of skin and keratinous fibres.

35. The process according to claim 34, wherein the dispersion of vesicles further comprises at least one second lipid which is different from the at least one ceramide of formula (I), and wherein an amount of the dispersion of vesicles formed in situ in the base composition is such that a total concentration of the at least one ceramide of formula (I) and the at least one second lipid in the final composition ranges from 0.05 to 15% by weight of the final composition.

36. The process according to claim 34, wherein the dispersion of vesicles further comprises at least one second lipid which is different from the at least one ceramide of formula (I), and wherein an amount of the dispersion of vesicles formed in situ in the base composition is such that a total concentration of the at least one ceramide of formula (I) and the at least one second lipid in the final composition ranges from 0.5 to 7.5% by weight of the final composition.

37. The process according to claim 1, wherein the joint use of the dispersion of vesicles and of the base composition comprises:
applying the dispersion of vesicles to said at least one of skin and keratinous fibres, in order to form a dispersion of vesicles film; and
applying the base composition to the dispersion of vesicles film.

\* \* \* \* \*